United States Patent [19]
Sandridge et al.

[11] Patent Number: 5,399,856
[45] Date of Patent: Mar. 21, 1995

[54] AMBIENT TEMPERATURE REFERENCE DEVICE

[75] Inventors: Robert L. Sandridge, Proctor; Robert N. Hunt, Wheeling, both of W. Va.

[73] Assignee: Miles Inc., Pittsburgh, Pa.

[21] Appl. No.: 132,728

[22] Filed: Oct. 6, 1993

[51] Int. Cl.6 .............................................. G01N 21/35
[52] U.S. Cl. .............................. 250/252.1; 250/339.08; 250/339.09; 250/339.13; 250/493.1; 356/346
[58] Field of Search ....................... 250/252.1 A, 493.1, 250/339.08, 339.09, 339.13, 338.5; 356/346

[56] References Cited

U.S. PATENT DOCUMENTS 4,795,253  1/1989  Sandridge et al. ................. 356/51
4,999,498  3/1991  Hunt et al. ....................... 250/338.5

OTHER PUBLICATIONS

Herget et al., "Remote Fourier Transform Infrared Air Pollution Studies", Optical Eng., 19 (4), Jul./Aug. 1980, pp. 508–514.

Primary Examiner—Carolyn E. Fields
Attorney, Agent, or Firm—Joseph C. Gil; Lyndanne M. Whalen

[57] ABSTRACT

A device for establishing an ambient temperature correction having (a) at least one reference surface which adequately represents the black body radiation spectrum of the air column between a long-path FTIR spectrometer and the infra-red source and (b) at least one means for shielding the reference surface from external sources of radiation gain or loss. In a preferred embodiment, the reference surface is made of thin metal having a blackened surface surrounded by an insulating shield. It is also preferred that a means for promoting positive air circulation across the reference surface or surfaces be included in the device of the present invention. This device is positioned in a location such that the field of view of the long-path FTIR spectrometer will be covered.

10 Claims, 4 Drawing Sheets

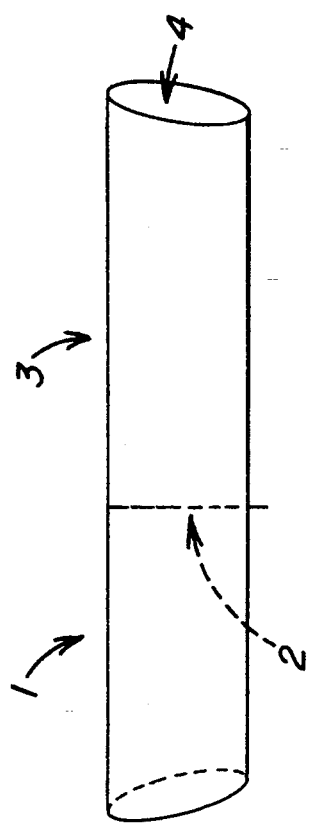
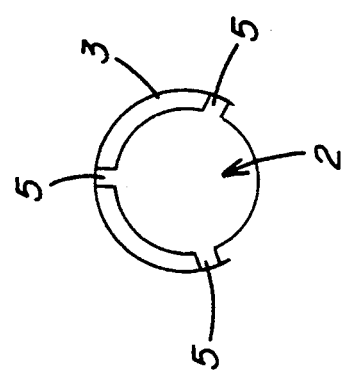
FIG. 1b
FIG. 1a

AMBIENT TEMPERATURE REFERENCE DEVICE

BACKGROUND OF THE INVENTION

The present invention relates to a device for establishing an ambient temperature correction for the results of gas analyses performed with a long-path Fourier Transform Infrared (FTIR) spectrophotometer and to the use of this device to obtain accurate and reproducible values.

Absorption spectra may be used to determine the presence and amounts of infra-red absorbing gases present in the atmosphere at selected locations. Such spectra are generated by collecting radiation from the selected location and subjecting this background radiation to FTIR analysis. Devices for generating emission spectra from such background radiation are known. See, for example, U.S. Pat. Nos. 4,795,253 and 4,999,498.

When used with a remote infra-red source (i.e., bistatic mode), these known devices typically employ spectra obtained from surfaces where the FTIR is located (e.g., a roof surface near the instrument, the side of a shaded wall, a grassy lawn, a hillside, the base plate of the instrument, etc.) to correct spectra taken with long-path FTIR instruments. However, it has been found that when the FTIR analyzer is used at longer distances or with weaker sources, spectra from such backgrounds are inadequate and introduce unacceptable errors. Similarly a constant temperature reference surface would not adequately reflect the ambient temperature of the selected location because such a surface would not reflect changes in air temperature from night to day or from winter to summer. It would, therefore, be advantageous to have a reference surface which adequately represents the radiation characteristics of the column of air through which the long-path FTIR is looking.

SUMMARY OF THE INVENTION

It is an object of the present invention to provide a device which represents the radiation characteristics of the column of air being analyzed by long-path FTIR.

It is also an object of the present invention to provide a device which establishes an ambient temperature correction that enables accurate and reproducible analyses of gaseous materials at selected locations by long-path FTIR.

It is a further object of the present invention to provide a method for using an ambient temperature correction device to obtain accurate and reproducible analyses by long-path FTIR.

These and other objects which will be apparent to those skilled in the art are accomplished by a device having (a) at least one reference surface which adequately represents the black body radiation spectrum of the air column between the instrument and the infra-red source and (b) at least one means for shielding the reference surface from external sources of radiation gain or loss in a preferred embodiment, the reference surface is made of thin metal having a blackened surface surrounded by an insulating shield. It is also preferred that a means for promoting positive air circulation across the reference surface or surfaces be included in the device of the present invention. This device is positioned in a location such that the field of view of the long-path FTIR spectrometer will be covered.

BRIEF DESCRIPTION OF THE DRAWINGS

FIGS. 1a and 1b illustrates a simple device within the scope of the present invention in which the reference surface is circular. FIG. 1a represents a side view of the inventive device and FIG. 1b represents a front view of this device.

FIG. 2a is a side view of the device in which one reference surface is present. FIG. 2b is a side view of the device in which two reference surfaces are present.

DETAILED DESCRIPTION OF THE PREFERRED EMBODIMENTS OF THE PRESENT INVENTION

Figure 2A:
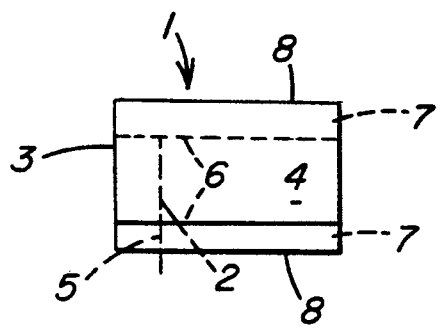
FIGS. 2a and 2b illustrate devices within the scope of the present invention in which insulation is present between the black body reference surface and the shield means.

The present invention relates to a device for establishing an ambient temperature correction which enables accurate and reproducible analysis of gaseous material in a selected location using long-path FTIR spectrophotometers. The present invention also relates to the use of this device in performing long-path FTIR spectroanalyses of gases present in the atmosphere at a selected location.

The device of the present invention is composed of (a) at least one heat conductive and radiating surface which adequately represents the black body radiation spectrum of the air column between the FTIR instrument and the remote infrared source and (b) at least one means for shielding this surface from sources of external radiation gain or loss. A surface adequately represents the black body radiation spectrum of the air column if its radiation spectrum essentially coincides with that of the remote infrared source in regions where 100% absorption of the radiation from the remote source has taken place as a result of infrared absorbing compounds in the optical path. Specific embodiments of devices within the scope of the present invention are illustrated in FIGS. 1a, 1b, 2a, 2b, 3 and 4 which will be discussed more fully below.

In the ambient correction device 1 illustrated in FIG. 1a and 1b the heat conductive and radiating reference surface 2 is a sheet of a material which is capable of assuming the temperature of the ambient air and of radiating energy which approximates a black body spectrum either as a result of its natural characteristics or as a result of a treatment such as blackening, e.g., by anodization. A plate (or plates) made from a material having high heat conductivity and a low mass is (are) particularly preferred. Any material having the ability to both conduct heat and radiate an approximate black body spectrum may be used to make the reference surface 2. Examples of suitable materials include: blackened or darkened aluminum, brass, copper, tin, steel, stainless steel or plastic. Thin sheets of blackened aluminum are particularly preferred.

Reference surface 2 may be of any size and shape. Reference surface 2 must, however, be sufficiently large enough to cover the field of view of the long-path FTIR spectrophotometer. It is advantageous to make the outer edges of reference surface 2 of such size and shape (e.g., with protruding tab(s)) that it (they) can be attached to the inside of shield 3.

Black body reference surface 2 is shown in FIG. 1a as being primarily surrounded by shield 3. Shield 3 must have an outer surface which is capable of reflecting radiant heat. Shield 3 must also be composed of a material that is capable of protecting reference surface 2 from heat gain or loss, due to anything but the ambient air. Shield 3 may be made of any material which is capable of reflecting heat. Shield 3 may be made of any material coated with a material capable of reflecting heat. Specific examples of suitable heat reflecting materials include: metals such as polished aluminum; white or light paint; aluminized or metallized plastic; white or light-colored plastic; and plastics such as expanded polystyrene or ABS copolymers. Reference surface 2 is mounted within shield 3 by mounting means 5. Any suitable mounting means may be used. In the device shown in FIG. 1, reference surface 2 is mounted by inserting tabs into slots located on the inside wall of shield 3.

Opening 4 allows ambient air to enter shield 3 and pass over reference surface 2. Opening 4 may be of any size which is larger than the infrared optical view of the instrument and which is sufficient to allow ambient air to pass over heat conductive surface 2. Opening 4 may be located at any position in ambient temperature correction device 1 which makes it possible for ambient air to pass over reference surface 2. It is preferred that the distance between the front of shield 3 to reference surface 2 be greater than 2 times the width of opening 4.

In the embodiment of ambient temperature correction device 1 illustrated in FIG. 2a, one black body reference surface 2 is mounted by mounting means 5 to shield 3. Reference surface 2 is blackened. The backside of reference surface 2 is reflective (i.e., not blackened). Shield 3 has outer reflective surfaces 8, inner walls 6 and insulation 7 positioned between outer surfaces 8 and inner walls 6. The walls of shield 3 may be joined together by any suitable means or they may be formed from a single insulated sheet of an appropriate material.

Figure 2B:
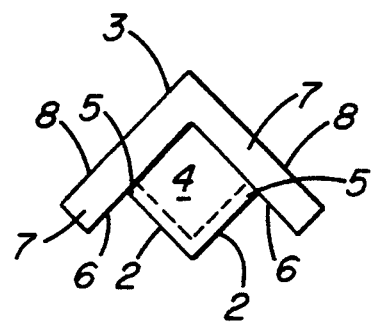

In the embodiment of ambient temperature correction device 1 illustrated in FIG. 2b, two black body reference surfaces 2 are mounted to shield 3. Shield 3 has outer heat reflective surfaces 8, inner wall 6, and insulation 7 positioned between outer surface 8 and inner wall 6. The two black body reference surfaces 2 may be bonded together or they may be formed by bending and cutting a single sheet of heat conductive material to form two perpendicular reference surfaces 2. Similarly the walls of shield 3 may be joined together by any suitable means or they may be formed from a single sheet of a material. The cross-section of shield 3 may be circular, square, polygonal, ellipsoidal or any other shape. The cross section of shield 3 may be closed or partially open. If the walls of shield 3 do not completely enclose reference surface 2, the opening may be of any size larger than the infrared optical view of the long-path FTIR spectrophotometer which allows ambient air to pass freely over the conductive reference surface 2. Insulation layer 7 may be made of any material known to have insulating properties. Examples of suitable insulating materials include: foams, fiberglass, air, cork, vacuum, wood or wood products, natural and synthetic fibers. Foams having a K factor of from about $$0.1 \text{ to about } 0.2 \frac{\text{BTU/inch}}{\text{ft}^2/\text{hr}/°F}.$$

are particularly preferred.

Any of the materials described above as being useful for making black body reference surface 2 and shield 3 of FIGS. 1a and 1b are also suitable for making black body reference surface 2 and shield walls 3 for the devices shown in FIGS. 2a and 2b.

Figure 3:
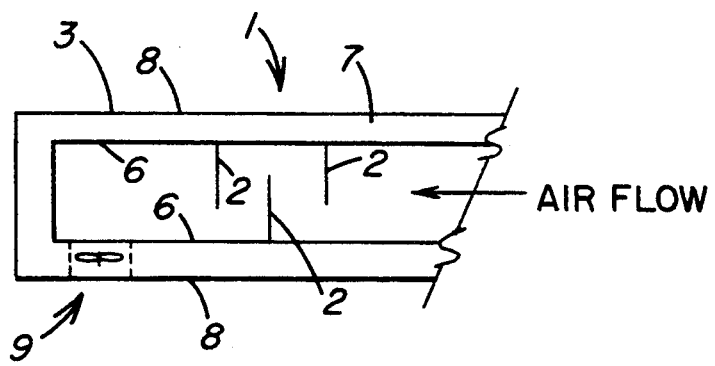
FIG. 3 illustrates a device within the scope of the present invention in which several black body reference surfaces are present and an exhaust fan is present to promote air circulation.

In FIG. 3, an ambient temperature correction device having three separate black body reference surface 2 positioned within heat shield 3 having insulation 7 is illustrated. The spacing of black body reference surface 2 must be such that ambient air may circulate over each black body reference surfaces 2. Air circulation may be promoted by air circulating means 9. Suitable air circulating means 9 is any device capable of circulating air over each black body reference surface 2. An exhaust fan is an example of suitable air circulating means. Air circulating means 9 may be positioned anywhere within the ambient temperature correction device 3 which will promote circulation of the air over black body reference surface 2, and not interfere with the FTIR instruments' view of reference surface 2. The preferred location for air circulating means 9 is behind the reference surface 2 as shown in FIG. 3. The exhaust fan may be electrically powered by conventional alternating current, by batteries, by solar cells or by a combination of these.

Figure 4:
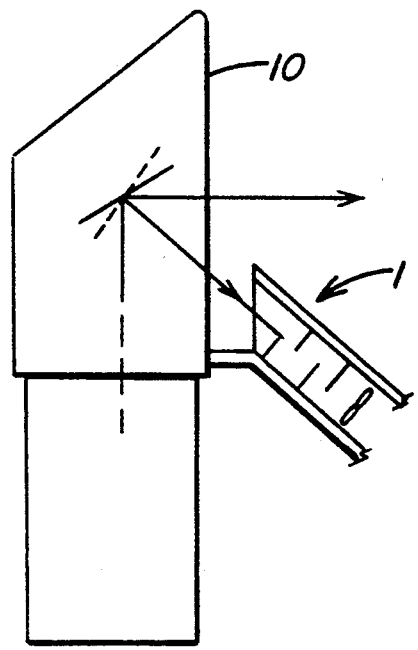
FIG. 4 illustrates the attachment of the device of FIG. 3 to a turret-type, long-path FTIR analyzer.

In FIG. 4, the ambient temperature correction device 1 illustrated in FIG. 3 is shown mounted on a radiation collection device 10 of the type described in U.S. Pat. No. 4,999,498. The position at which the device of the present invention is mounted onto the radiation collection device 10 should be such that the black body reference surface 2 will cover the field of view of the radiation collection device. It is, however, also possible that the ambient temperature correction device of the present invention may be used without mounting it directly to the radiation collection device. The device of the present invention may in principle be placed at any distance from the FTIR spectrophotometer such that the black body reference surface 2 covers the field of view of the infrared instrument. In practice, distances not exceeding 20 feet are preferred to facilitate aiming.

Having thus described our invention, the following Example is given as being illustrative thereof. All pads are pads by volume, unless otherwise indicated.

EXAMPLES

Example 1

A device corresponding to that illustrated in FIG. 3 was constructed as follows:

| | |
|---|---|
| Reference surfaces 2: | sheets of aluminum having a thickness of 12 mils and a front surface which had been blackened with non-reflective black paint; |
| Heat reflective surfaces 3: | white PVC pipe having a wall thickness of ⅛ inch; |
| Insulation 7: | a CFC-11 blown rigid polyurethane foam having a K factor of about $0.12 \frac{\text{BTU/inch}}{\text{ft}^2/\text{hr}/°F}$ |

| Air circulation means 9: | an exhaust fan which is commercially available from Radio Shack division of Tandy Corporation as item 273-242. This device was mounted on a camera tripod to assist in positioning and aiming. |
|---|---|

The device was placed at distances from 2 to 20 feet from the gas analyzer of the type marketed by the Hennecke Instrument Group of Miles Inc. as an "FTIR Remote Gas Analyzer" to determine the accuracy and reproducibility of measurements made with the device of the present invention as compared to measurements made using only ambient surfaces as reference points or no ambient correction.

Figure 5:
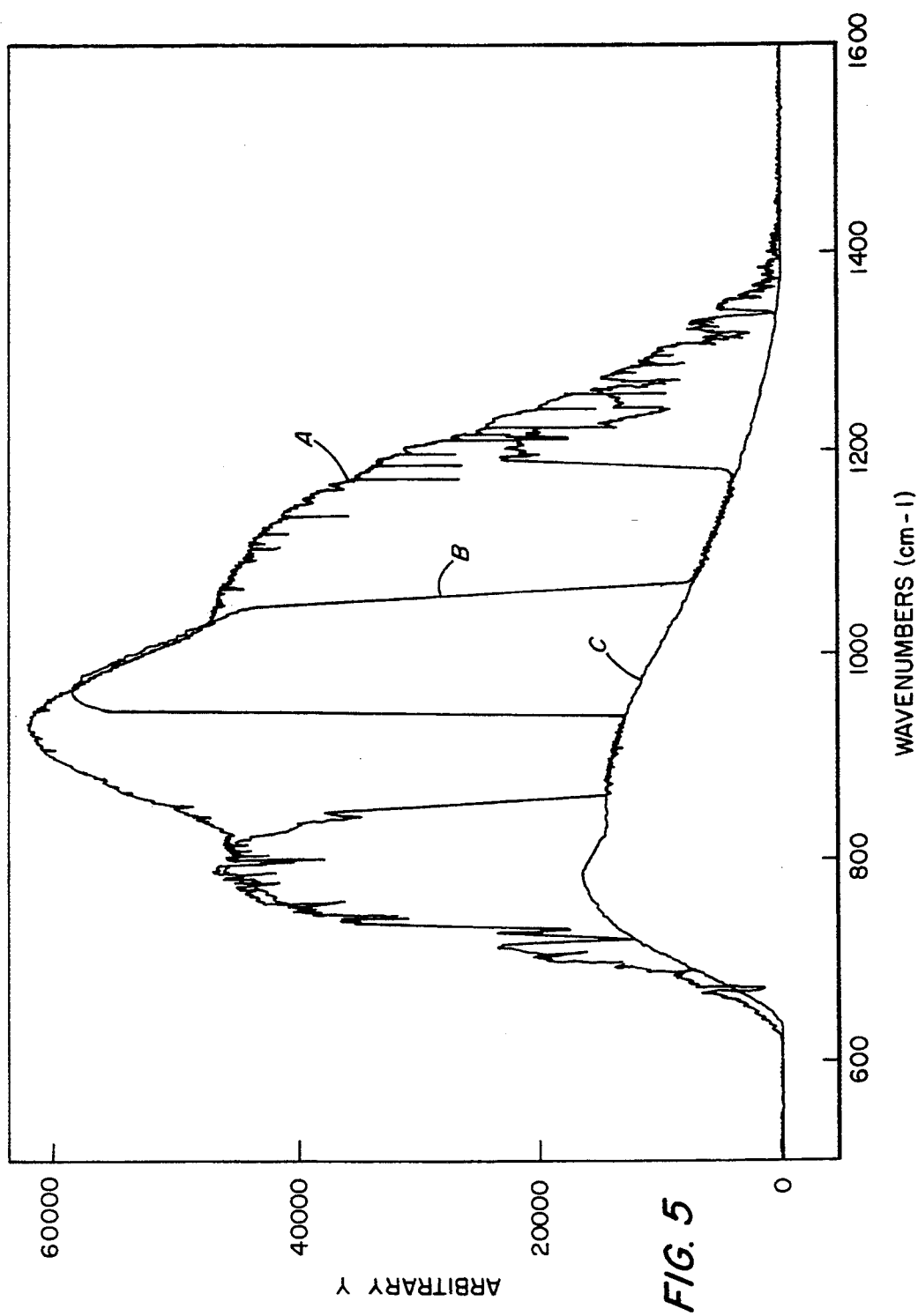
FIG. 5 is a plot of the curves generated from 64 time averaged spectra in tests described in the Example.

A long-path FTIR spectrometer of the type marketed by the Hennecke Instrument Group of Miles, Inc. as an "FTIR Remote Gas Analyzer" was used to analyze the atmosphere in the vicinity of a large industrial installation. A remote FTIR source of the type described in U.S. Pat. No. 5,003,184 was positioned about 50 meters from the FTIR Remote Gas Analyzer. The device corresponding to that shown in FIG. 3 was positioned about 2 feet from the gas analyzer so that reference surfaces 2 faced directly into the infrared optical path of the gas analyzer. An empty 2.5 cm. gas calibration cell having transparent polyethylene windows was positioned in the infrared optical path of the FTIR instrument and a curve (curve A of FIG. 5) made up of 64 time averaged spectra was obtained. The cell was then filled with CFC-12 (dichlorodifluoromethane) and a curve (curve B of FIG. 5) made up of 64 time averaged spectra was obtained. Curve B clearly shows two strong absorption bands which exhibit essentially 100% absorption of the energy from the remote infrared source. Curve C was obtained by aiming the gas analyzer (with the calibration cell in place) at the ambient temperature correction device of the present invention and collecting 64 time averaged spectra. Curve C coincides with the 100% absorption areas of curve B, thus demonstrating tile ability of the device of the present invention to provide a suitable ambient reference curve for the correction of long-path FTIR spectrometers operated with a remote infrared source.

Figure 6:
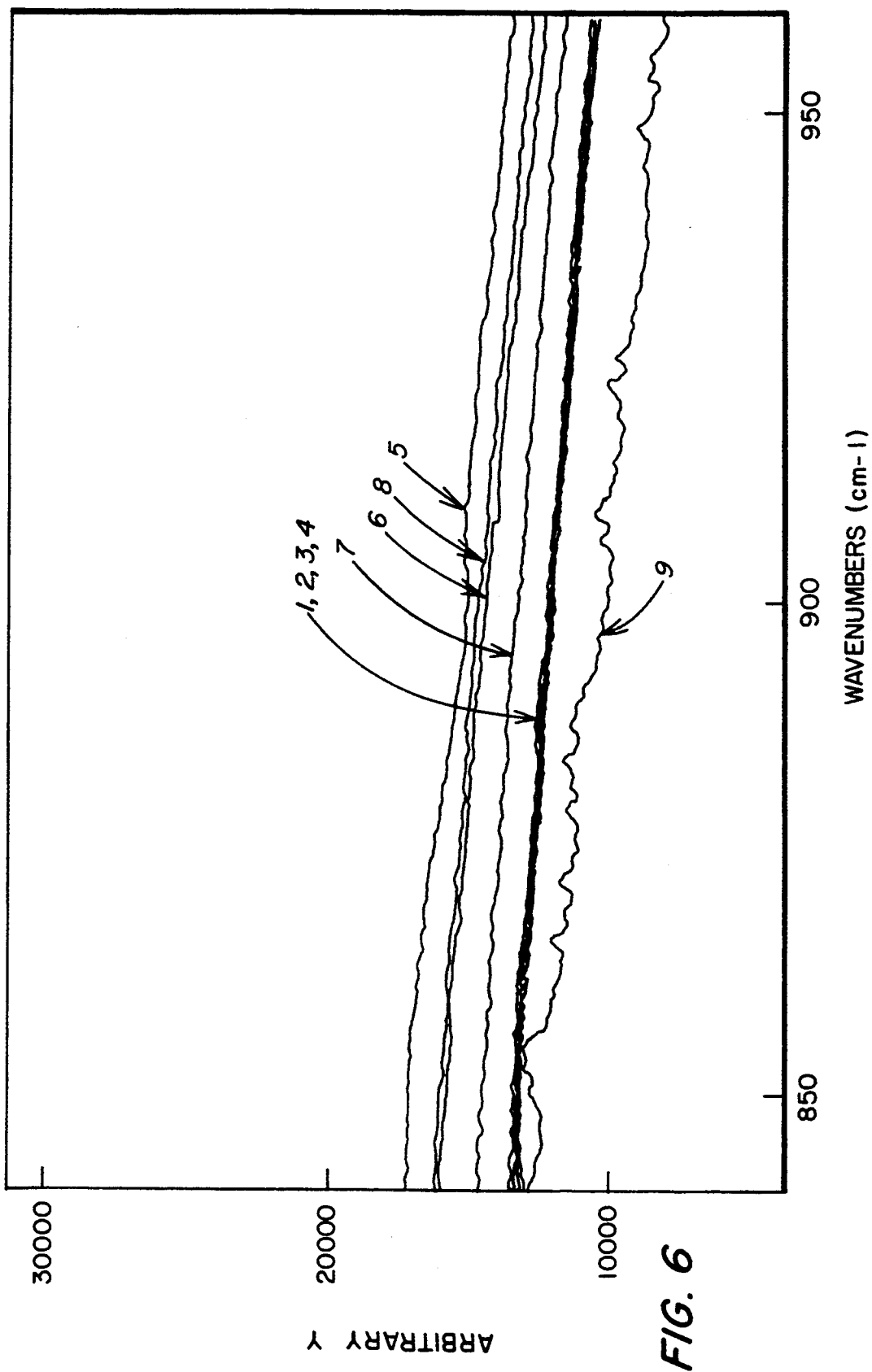
FIG. 6 illustrates spectra of several ambient surfaces in the vicinity of the long-path FTIR instrument during the tests described in the Example.

FIG. 6 has an expanded wave number scale on which is shown spectra of several other ambient surfaces in the vicinity of the instrument (i.e., hillside with trees, shaded building wall, parking lot and gravel roof) compared with 4 spectra taken using the device of the present invention. Table 1 demonstrates the magnitude of the error caused in the transmission value which would be caused if an improper or no ambient correction were employed. The value shown is measured at 900 cm$^{-1}$ and against a remote source 330 meters from the instrument. This condition represents measurements made at longer distances against sources of moderate (e.g., 45 watt) power. Although stronger sources at closer distances may somewhat reduce the relative error caused by using an improper ambient reference, the best quantitative measurements can be made only when a proper ambient correction is made.

In Table 1, the reported transmission units are taken from the transmission spectra generated by the instrument. These units represent the number of data points collected at a particular wave number and reflect the energy received at the detector.

TABLE 1

| Spectrum (FIG. 6) | Background Type | Instrument Transmission Units, T (measured at 900 cm$^{-1}$) | Error in T %* |
|---|---|---|---|
| 1 | Device in FIG. 3 | 12062 | +0.3 |
| 2 | Device in FIG. 3 | 12148 | −0.2 |
| 3 | Device in FIG. 3 | 12154 | −0.2 |
| 4 | Device in FIG. 3 | 12100 | +0.1 |
| 5 | Gravel roof | 15063 | −15.3 |
| 6 | Shaded building wall | 14362 | −11.6 |
| 7 | Wooded hillside | 13260 | −5.9 |
| 8 | Parking lot | 14645 | −13.1 |
| 9 | Hazy sky | 10031 | +10.8 |
|  | No correction | 0 | +62.8 |

*Correct value for T for ambient energy was 12116 (average of T for spectra 1–4).

T of 31414 was transmission value obtained at 900 cm$^{-1}$ against a remote source 330 meters distant from the gas analyzer and represents the energy available under those conditions for making the measurement.

$$\% \text{ error} = \left( \frac{31414 - T}{31414 - 12116} \times 100 \right) - 100$$

Although the invention has been described in detail in the foregoing for the purpose of illustration, it is to be understood that such detail is solely for that purpose and that variations can be made therein without departing from the spirit and scope of the invention except as it may be limited by the claims.

What is claim:

1. A device which is an ambient temperature reference for a long-path Fourier transform infrared spectrophotometer used to analyze a gas comprising:
    (a) a heat conductive surface which approximates the black body radiation spectrum of an air column between the spectrophotometer and an infrared source, and
    (b) means for shielding the heat conductive surface from sources of radiation gain or loss.

2. The device of claim 1 in which a) is an aluminum sheet having a blackened surface.

3. The device of claim 1 in which the means for shielding the heat conductive surface b) is made of a heat reflective material.

4. The device of claim 1 in which an insulator is positioned between a) and b).

5. The device of claim 4 in which the insulator is selected from the group consisting of air, rigid or flexible foams, vacuum, cork, inorganic insulating materials, and wood or wood products.

6. The device of claim 1 in which the heat conductive surface is made of a material having a blackened surface selected from the group consisting of aluminum, copper, zinc, nickel, chromium, or heat conductive metal alloys.

7. The device of claim 1 in which the shielding means b) is made of a material selected from the group consisting of thermoplastic or thermoset resins, fiber-reinforced polymers, foamed plastics, pressed paper, bonded wood products, glass and metals.

8. The device of claim 1 in which a means for circulating ambient air so that it passes over the heat conductive surface a) is included.

9. The device of claim 8 in which the circulating means is an exhaust fan.

10. A method for correcting for ambient temperature the analytical results obtained by a long-path Fourier transform infrared spectrophotometer comprising placing the device of claim 1 in a location such that the heat conductive surface will be in the field of view of the spectrophotometer, collecting radiation from that heat conductive surface, and analyzing the infrared radiation collected from this surface with the spectrophotometer.

* * * * *